United States Patent [19]

Ochiai et al.

[11] 4,363,794

[45] Dec. 14, 1982

[54] ORAL COMPOSITION FOR CARIES PROPHYLAXIS

[75] Inventors: Yoshihito Ochiai, Fujisawa; Syozi Nakashima, Yamanishi, Japan; Midori Hayashi, Yamakita, all of Japan

[73] Assignee: Lion Corporation, Tokyo, Japan

[21] Appl. No.: 949,031

[22] Filed: Oct. 6, 1978

[30] Foreign Application Priority Data

Oct. 20, 1977 [JP] Japan .............................. 52/126102

[51] Int. Cl.³ .................... A61K 7/18; A61K 31/19; A61K 7/16; A61K 33/42
[52] U.S. Cl. ...................................... 424/52; 424/49; 424/57; 424/128; 424/151; 424/317
[58] Field of Search .................. 424/52, 49, 131, 151, 424/128, 57, 317

[56] References Cited

U.S. PATENT DOCUMENTS

| | | | |
|---|---|---|---|
| 2,876,167 | 3/1959 | Manahan | 424/52 |
| 2,946,725 | 7/1960 | Norris et al. | 424/52 |
| 3,105,798 | 10/1963 | Holliday et al. | 424/52 |
| 3,175,951 | 3/1965 | Tucker et al. | 424/52 |
| 3,227,617 | 1/1966 | Manahan et al. | 424/52 |
| 3,227,618 | 1/1966 | Manahan et al. | 424/52 |
| 3,235,459 | 2/1966 | Francis | 424/52 |
| 3,266,867 | 8/1966 | Muhler | 424/52 |
| 3,282,792 | 11/1966 | Fiscella | 424/52 |
| 3,544,678 | 12/1970 | Griebstein | 424/52 |

FOREIGN PATENT DOCUMENTS 804486  11/1958  United Kingdom ................. 424/52

Primary Examiner—Douglas W. Robinson
Attorney, Agent, or Firm—Birch, Stewart, Kolasch & Birch

[57] ABSTRACT

An oral composition is disclosed which comprises a stannous salt such as stannous fluoride, a water-soluble fluoride salt such as sodium fluoride and an orally acceptable acid such as L-ascorbic acid, lactic acid, malonic acid, tartaric acid, citric acid, hydrochloric acid and pyrophosphoric acid, the molar ratio of fluoride ion to stannous ion being in the range of 3.2 to 7:1, preferably 3.5–6:1, in an aqueous condition and the pH of the composition being in the range of from 2 to 4. The composition exhibits excellent effects on the inhibition of dental caries.

8 Claims, 14 Drawing Figures

ORAL COMPOSITION FOR CARIES PROPHYLAXIS

BACKGROUND OF THE INVENTION

1. Field of the Invention

The present invention relates to oral compositions such as topical solutions or pastes for application in the dental office, cavity sealers, gels for ultrasonic treatment, mouthwashes, prophylactic pastes, dentifrices, dental flosses and desensitizers of teeth. More particularly it relates to oral compositions containing stannous salts and water-soluble fluoride salts, and having the effect of inhibition of dental caries upon application.

2. Description of the Prior Art

Fluoride compounds have found widespread usage as effective ingredients for inhibiting dental caries. The addition of those fluoride compounds to drinking water, toothpastes, topical solutions and the like has been successful in the reduction of dental caries. Among those fluoride compounds, fluoride salts which contain stannous ions (e.g. stannous fluoride) have been reported to cause an increase in the fluoride uptake by the dental enamel and consequently in acid-resistance of the enamel after treatment as compared with fluoride salts which do not contain stannous ions (e.g. sodium fluoride). This fact suggests that fluoride salts with stannous ions are effective for reducing dental caries. Recently, it has also been reported that a highly insoluble film or deposits of $Sn_3F_3PO_4$ are formed on the tooth surface, such film or deposits coming from the reaction of stannous fluoride with $HPO_4^{2-}$ ion which has been formed from dissolution of part of the enamel by bringing the tooth surface into contact with an aqueous solution containing stannous fluoride for an extended period of time.

However, the fluoride compounds providing stannous ions such as stannous fluoride are chemically unstable. In the situation of an aqueous solution containing stannous fluoride as an example, its stability during storage and under heat deteriorates rapidly, followed by ready occurrence of insoluble, whity precipitants which are amorphous substances such as stannous oxide, stannous hydroxide and the like. This is less reactive with the dental enamel. Due to the gradual decrease in the effectiveness during storage, stannous fluoride becomes unsuitable as a dental caries inhibitor.

It has been the conventional practice to maintain stannous ions in a stable, available condition for easy reaction with the enamel. One means lies in the addition of any acid or acids in a relatively large quantity such that an oral composition may have a pH of less than 2. Low pH (below 2) in the composition, however, creates an obstacle to oral acceptability since it is excessively acidic. The other means is to mask the stannous ions with the aid of any chelating agent or agents such as EDTA, pyrophosphates and tripolyphosphates, and to thereby minimize hydrolysis of the stannous compounds. Such chelating agent or agents are liable to provide very stable complexes with the stannous ions, resulting in decreased availability of free or active stannous ions which are effective for inhibiting dental caries.

More advanced means have been proposed to surmount the above noted difficulties. U.S. Pat. No. 3,105,798 discloses a dentifrice composition consisting essentially of a water-soluble fluoride salt, stannous tin and a water-soluble source of six carbon aldonate groups capable of forming water-soluble complexes with stannous tin, the molar ratio of the aldonate group to stannous tin being in the range of from about one:one to about three:one, the molar ratio of stannous tin to fluoride ions being greater than one:one, said dentifrice having a pH of from about 5 to 7. Crystals of sodium pentafluorostannite ($NaSn_2F_5$) obtained by reacting one mole of sodium fluoride with two moles of stannous fluoride are described in U.S. Pat. No. 3,490,866. These known oral compositions have not been widely recognized in effectiveness in the reduction of dental caries. The use of stannous salts of polyphosphonic acids such as methanediphosphonic acid or ethane-1-hydroxy-1, 1-diphosphonic acid described in U.S. Pat. No. 3,549,677 is also deficient in that production of the stannous salts of polyphosphonic acids is complicated and expensive.

The prior art compositions containing stannous ions and fluoride ions are effective to some extent for dental caries reduction, but their effectiveness is not so extremely high. Moreover, they require repeated application because of their lower reactivity to the tooth surface upon application or readily decreased retention of effectiveness.

Accordingly, an oral composition should be expected which possesses excellent effects on the inhibition of dental caries and which retains its effectiveness for an extended length of time without repeated application.

SUMMARY OF THE INVENTION

It is, therefore, an object of the present invention to provide a novel oral composition which is extremely effective for inhibiting dental caries and which has a prolonged effectiveness after application.

Another object of this invention is to provide an oral composition which can maintain stannous ion in a stable and available condition for the reduction of acid solubility of the enamel.

According to the present invention, there is provided an oral composition comprising a stannous salt, a water-soluble fluoride salt and an orally acceptable acid, the molar ratio of fluoride ion to stannous ion being in the range of from 3.2:1 to 7:1 in an aqueous condition. The oral composition having the above-mentioned range of the molar ratio is capable of increasing the acid-resistance of the treated enamel, which is highly related to prevention of dental caries.

According to a preferred embodiment of the present invention, the orally acceptable acid is added in such a manner that the pH of the composition is in a range of 2 to 4. The composition of the preferred embodiment, which has a pH of from 2 to 4, has an excellent effect on the increment of acid-resistance of the enamel. It can form on the tooth surface a highly insoluble film or deposits which are resistant to detachment as would often arise from brushing or food chewing. Such film or deposits afford increased uptake of fluoride by the enamel and decreased acid-solubility of the enamel. More specifically, the tooth coated with the film or deposits contains 15,000 ppm of fluoride ion at its surface (3 $\mu$m in depth). Further, the hardness (Vickers Hardness Number) of the enamel surface treated with the composition is 280 to 290 even after decalcification with an acid. These hardness values are surprisingly high since an untreated enamel (control) after decalcification in a similar way is at most 80 in Vickers hardness. The composition of the preferred embodiment ensures dental caries inhibiting effects to an extremely high level, and can also maintain the stannous ion in a stable or active form available for the reduction of acid-solubility of the dental enamel over a long period of time.

The above and other objects, features and advantages of this invention will become more apparent and understandable from the following detailed description, experimental examples, examples and claims.

DETAILED DESCRIPTION OF THE INVENTION

Suitable stannous salts useful in the present invention include stannous fluoride, stannous chloride, stannous chlorofluoride, stannous pyrophosphate, stannous monofluorophosphate and stannous acetate. In general, stannous fluoride is preferably used. The quantity of the stannous salt in the present composition depends upon any useful forms of the composition, but the stannous salt should be dissolved in water together with any applicable water-soluble fluoride salt or salts so that the stannous salt sets an upper limit to its saturated state. The lower limit content of the stannous ion should preferably be about 0.07% by weight of the total amount of the composition in order to allow the effect of the stannous ion to be more greatly exhibited.

As for stannous fluoride, the total stannous fluoride content should be in the range of from 0.1 to 6% by weight based on the composition.

Suitable water-soluble fluoride salts include inorganic fluoride salts such as sodium fluoride, potassium fluoride, lithium fluoride, cesium fluoride, zirconium fluoride, ammonium fluoride, sodium monofluorophosphate and potassium monofluorophosphate, and organic fluoride salts such as hexylamine hydrofluoride, laurylamine hydrofluoride, cetylamine hydrofluoride, glycinamine hydrofluoride, lysine hydrofluoride and alanine hydrofluoride. In practice, these fluoride salts may be used singly or in combination.

Of the above fluoride salts, sodium fluoride, potassium fluoride, ammonium fluoride, sodium monofluorophosphate, potassium monofluorophosphate and cetylamine hydrofluoride are particularly suitable for this invention in view of good oral acceptance and good water-solubility in the above condition. The selected fluoride salts are neutral and very stable.

According to the present invention, the stannous salt and the water-soluble fluoride are dissolved together in water such that the fluoride ion has a ratio of 3.2 to 7 moles to one mole of stannous ion in an aqueous condition. This ratio of the fluoride ion to the stannous ion causes a significant increase in acid-resistance of the enamel. A ratio below the above specified limit, which means insufficient fluoride salt in the composition, detrimentally affects both the acid-resistance and the reservation of the stannous ion in a stable condition. A ratio above such limit, which means excessive fluoride salt, exerts inadverse effects on the acid-resistance. For these reasons, the ratio of the fluoride ion to the stannous ion should be in the range of from 3.2 to 7:1, preferably from 3.5 to 6:1. If the present composition is for use as a toothpaste, the total fluoride ion is preferably not more than 1,100 ppm.

While the composition containing the stannous salt and the water-soluble fluoride salt in an aqueous condition in the ratio of 3.2 to 7 moles of fluoride ion per mole of stannous ion is in a substantially acidic state, it is necessary to add at least one orally acceptable acid to the mixture of the stannous salt and the fluoride salt. When a tooth is treated with the acid-containing composition, a film is formed on the tooth surface in a short length of time, for example, within about 30 seconds.

The film thus obtained is highly insoluble and resistant to physical abuse such as brushing, thereby assuring firm attachment to the tooth. The film can protect the outer enamel even after decalcification with an acidic solution from deterioration in hardness. More advantageously, since the film serves to considerably decrease the quantity of $Ca^{2+}$ eluting from the enamel, the tooth enamel does not involve any destruction on its surface even after decalcification with an acidic solution at pH 4.5. The treatment with the composition containing the orally acceptable acid results in improvement in the quality of the tooth and in increase of the caries inhibiting effect.

As a result of the study leading to the present invention, it has been confirmed that when a tooth is treated with the acid-containing composition, slight etching occurs in the tooth surface, and part of the enamel dissolves from the etched tooth portion, thus introducing $Ca^{2+}$ and $HPO_4^{2-}$ ions. The $Ca^{2+}$ ion forms relatively insoluble $CaF_2$ in cooperation with $F^-$ ion, whereas the $HPO_4^{2-}$ ion forms with $Sn^{2+}$ and $F^-$ ions fairly insoluble $Sn_3F_2PO_4$ which eventually produces the film on the tooth surface. In the case where stannous fluoride is used alone, such phenomena do not take place within a shortened period of time.

Suitable orally acceptable acids include monocarboxylic acids, dicarboxylic acids, tricarboxylic acids and mineral acids. In practice, these orally acceptable acids may be used singly or in combination. Suitable monocarboxylic acids are L-ascorbic acid, lactic acid, acetic acid, propionic acid, n-butyric acid and gluconic acid. Especially preferable are L-ascorbic acid, lactic acid and gluconic acid because of their good action to stabilize stannous ion. Suitable dicarboxylic acids include malonic acid, tartaric acid, malic acid, succinic acid, maleic acid, L-aspartic acid, L-glutamic acid and oxalic acid. Especially preferable are malonic acid and tartaric acid for the same reason mentioned above. A suitable tricarboxylic acid is citric acid. Hydrochloric acid, sulfuric acid, orthophosphoric acid and pyrophosphoric acid are suitable mineral acids. Especially preferable are hydrochloric acid and pyrophosphoric acid for the same reason mentioned above.

The orally acceptable acid or acids are mixed so that the pH of the composition should lie between 2 and 4. The specified pH range results in an increase of effectiveness on the increment of acid-resistance for the treated enamel and on stability of the stannous ion. Low pH (below 2) tends to pose an obstacle to oral application of the composition. A pH above 4 often causes reduced availability and stability of stannous ion.

More preferably, the molar ratio of any selected one monocarboxylic acid lies between $0.8 \times 0.5^n$ and $30 \times 0.6^n$ on the basis of one mole of stannous ion, wherein the exponent "n" represents the weight percent of the stannous ion in the composition. The molar ratio within the above specified limit corresponds to an area defined between the straight lines $X_1$ and $X_3$ in FIG. 5. The preferable molar ratio of any one acid selected from the dicarboxylic acids, tricarboxylic acids and mineral acids lies between $0.2 \times 0.6^n$ and $5 \times 0.6^n$ on the basis of one mole of stannous ion, such molar ratio limit being equivalent to an area defined between the straight lines $Y_1$ and $Z_1$ in FIG. 10. Above or below said molar ratio limit results in reduced resistance to acid attack. Especially, below the lower limit gives declined stability of the stannous ion.

Figure 5:
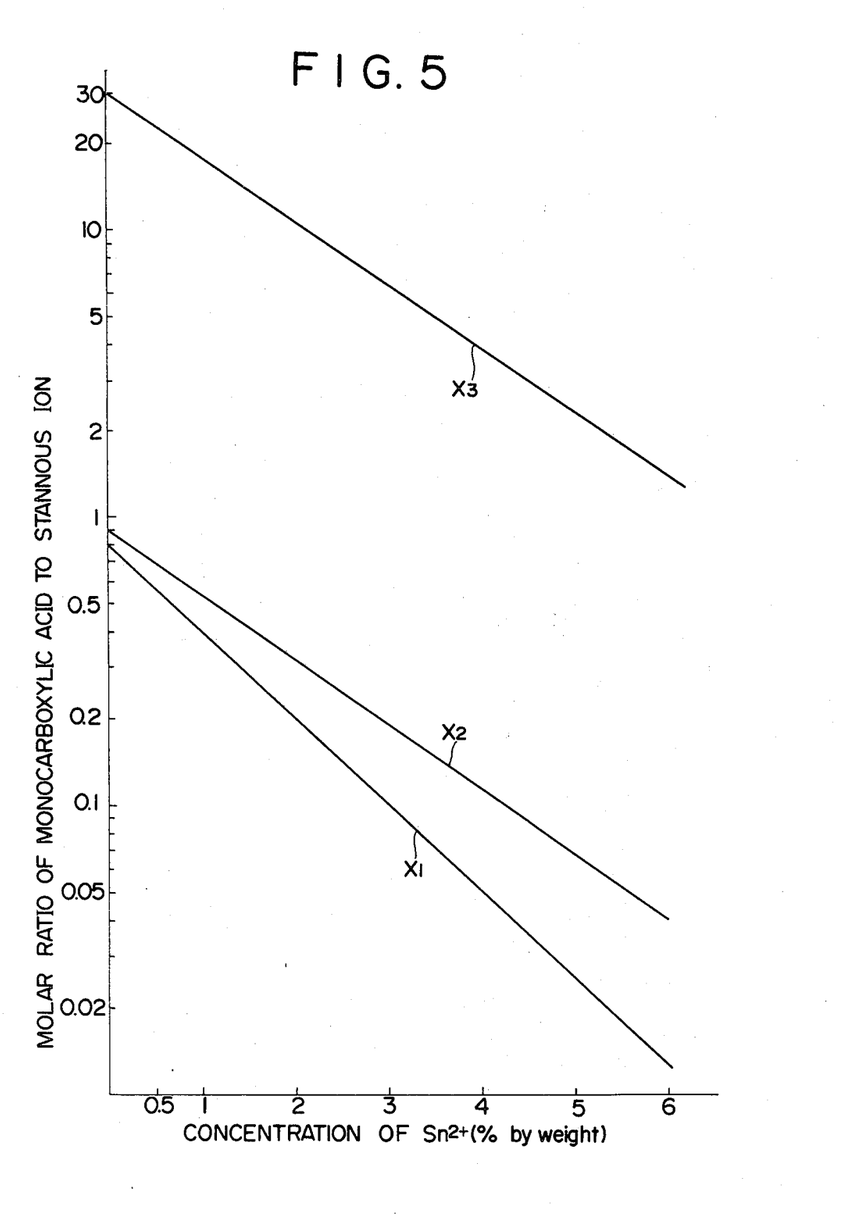
FIG. 5 is a graph showing the preferable range of the molar ratio of monocarboxylic acid to stannous ions in relation to the concentration of stannous ions.

The above specified molar ratio limit of the monocarboxylic acids should more preferably be in the range of from $0.9 \times 0.6^n$ to $30 \times 0.6^n$, an area defined between straight lines $X_2$ and $X_3$ in FIG. 5. The above specified molar ratio limit of the dicarboxylic acids, tricarboxylic acids and mineral acids should more preferably be in the range of from $0.3 \times 0.6^n$ to $3 \times 0.5^n$, which range is equivalent to an area defined between straight lines $Y_2$ and $Z_2$ in FIG. 10.

The oral compositions of the present invention may be used as topical solutions or pastes for dental use, cavity sealers, gels for ultrasonic treatment, mouthwashes, prophylactic pastes, dentifrices, dental flosses, desensitizers of teeth and the like. In the manufacture of the present compositions, the stannous salt, the water-soluble fluoride salt and at least one orally acceptable acid are dissolved in water. To this mixture are added any other ingredients which are common in the production of those oral compositions.

In case of preparing the composition in the form of a solution, for example, for use as a topical solution or a mouthwash, the stannous salt and the water-soluble fluoride salt are dissolved in distilled or deionized water together with the orally acceptable acid. To this mixture are added a sweetening agent such as saccharin and a flavor. As for the composition in the form of a paste such as a topical paste, a humectant such as glycerin and a binder such as xanthane gum are added to the above obtained mixture containing a sweetening agent and a flavor. For preparing the composition for use as a toothpaste, additives include an abrasive such as calcium pyrophosphate, insoluble calcium polyphosphate, insoluble sodium metaphosphate, titanium dioxide, resins, calcium sulfate, aluminum hydroxide and anhydride silica in a range of from 20 to 60% by weight of the total of the composition, a binder such as xanthane gum, guar gum, carrageenan and sodium carboxymethyl cellulose in a range of from 0.5 to 5% by weight, a humectant such as glycerin, sorbitol and other polyhydric alcohols in a range of from 20 to 25% by weight, a foaming agent such as water-soluble alkyl sulfates including sodium lauryl sulfate in a range of from 1.5 to 3% by weight, a flavor such as peppermint oil, spearmint oil and anise oil, a sweetening agent such as saccharin, an antiseptic agent such as ethyl para-hydroxybenzoate and butyl parahydroxybenzoate, an anticariogenic agent such as chlorhexidine and any other ingredients.

According to the present invention, the effective protection from occurrence of dental caries can be achieved. Of importance, a highly insoluble, firm film is formed on the tooth surface, whereby the effectiveness on the inhibition of dental caries is prolonged upon only one application. Therefore, the repeated treatment with the composition may not be required.

Amalgams, composite resins and the like have hitherto been utilized for restoration of dental caries. However, the tooth filled as for example with such amalgams causes any appreciable gap or spacing into which bacteria would invade, thereby resulting in recurrent caries. The present composition is also effective as a cavity sealer for such gap. Mere application of this composition to the cavity is sufficient to produce a highly insoluble and caries-resistant film which can firmly adhere to the tooth and which is not subject to physical shocks or friction within the cavity for a long period of time.

The composition maintains the stannous ion in a stable condition for an extended period of time. In this composition for use as topical solutions or mouthwashes, the stannous ion is held sufficiently stable even in a low concentration as compared with any conventional oral compositions. Thus, the composition retains dental caries inhibiting effects even after its prolonged storage. Due to improved stability to aging and heat, the composition having a high concentration of stannous ion can be stored as a supply and may be diluted for practical use.

The invention is hereinafter described more specifically in terms of several experimental examples.

EXPERIMENTAL EXAMPLE 1

100 g of each of some test compositions was prepared by dissolving 0.27 g of stannous fluoride and a given amount of sodium fluoride and L-ascorbic acid in water such that the molar ratios of fluoride ions to stannous ions and of the L-ascorbic acid to the stannous ions were given variable amounts in the compositions. Sample teeth were immersed in the compositions at 50° C. for 3 minutes, and then washed with running tap water for 1 hour. Each sample tooth was brushed ten times in both the longitudinal and transverse directions, respectively, whereby any loosely attached deposits on the enamel were removed. These teeth were then subjected to decalcification in an acidic solution (0.1 M acetic acid buffered solution of pH 4.5) at 20° C. for 2 hours. After decalcification, the Vickers hardness was measured on the enamel surface of each of the sample teeth, and the hardness values were set as indices for the resistance to acid-solubility of the enamel.

The results obtained are shown in Tables 1 and 2. These results are further illustrated in FIGS. 1 and 2, respectively.

Next, 100 g of each of some test compositions was prepared by dissolving 1.0 g or 3.0 g of stannous fluoride and a given amount of sodium fluoride and L-ascorbic acid in water. After sample teeth were treated as above, the Vickers hardness was measured on the sample teeth. The results obtained are shown in Table 3 and FIG. 2.

Each hardness value is the average of five measurements.

The following are the definitions of the symbolic valuation systems in Table 1 and subsequent tables:
⊚: Extremely excellent in both enamel solubility reduction and composition stability;
○: Good in both enamel solubility reduction and composition stability;
Δ: Slightly inferior in either of enamel solubility reduction or composition stability;
X: Worse in either or both of enamel solubility reduction and composition stability.

EXPERIMENTAL EXAMPLE 2

100 g of each of some test compositions was prepared by dissolving 0.27 g of stannous fluoride and a given amount of sodium fluoride and lactic acid in water. After sample teeth were treated as in Experimental Example 1, the Vickers hardness was measured on the sample teeth. The results obtained are shown in Tables 4 and 5. These results are further illustrated in FIGS. 3 and 4, respectively.

TABLE 1

Figure 1:
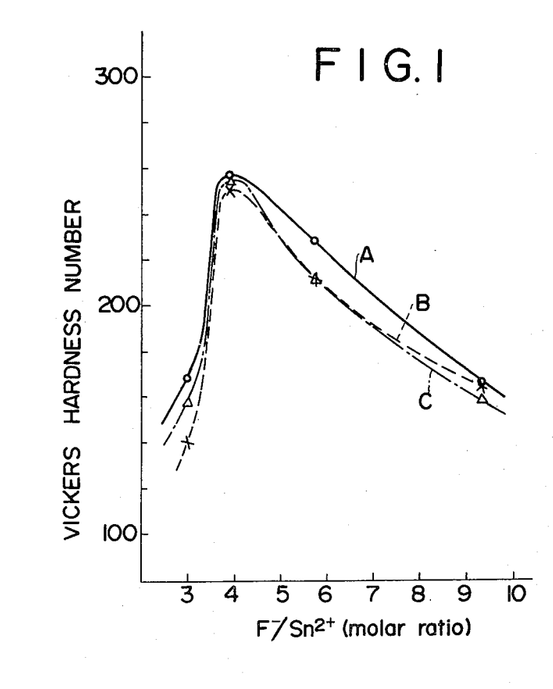
FIG. 1 is a graph showing the relationship between the molar ratios of fluoride ions to stannous ions in the test compositions obtained by dissolving stannous fluoride, sodium fluoride and L-ascorbic acid into water and the hardness of the decalcified teeth surfaces treated with these compositions.

| Content of L-ascorbic acid (g) | L-ascorbic acid/$Sn^{2+}$ (molar ratio) | Content of NaF (g) | $F^-/Sn^{2+}$ (molar ratio) | pH of Composition | Hardness (VHN) | Evaluation | Reference mark in FIG. 1 |
|---|---|---|---|---|---|---|---|
| 7.96 | 26.2 | 0.53 | 9.3 | 2.9 | 166 | X | A |
| " | " | 0.27 | 5.7 | 2.4 | 226 | ⊚ | |
| " | " | 0.14 | 3.9 | 2.4 | 257 | ⊚ | |
| " | " | 0.07 | 3.0 | 2.3 | 168 | X | |
| 3.98 | 13.1 | 0.53 | 9.3 | 3.2 | 165 | X | B |
| " | " | 0.27 | 5.7 | 2.6 | 212 | ⊚ | |
| " | " | 0.14 | 3.9 | 2.6 | 250 | ⊚ | |
| " | " | 0.07 | 3.0 | 2.5 | 140 | X | |
| 2.0 | 6.6 | 0.53 | 9.3 | 3.8 | 161 | X | C |
| " | " | 0.27 | 5.7 | 3.4 | 210 | ⊚ | |
| " | " | 0.14 | 3.9 | 2.8 | 257 | ⊚ | |
| " | " | 0.07 | 3.0 | 2.6 | 158 | X | |

TABLE 2

Figure 2:
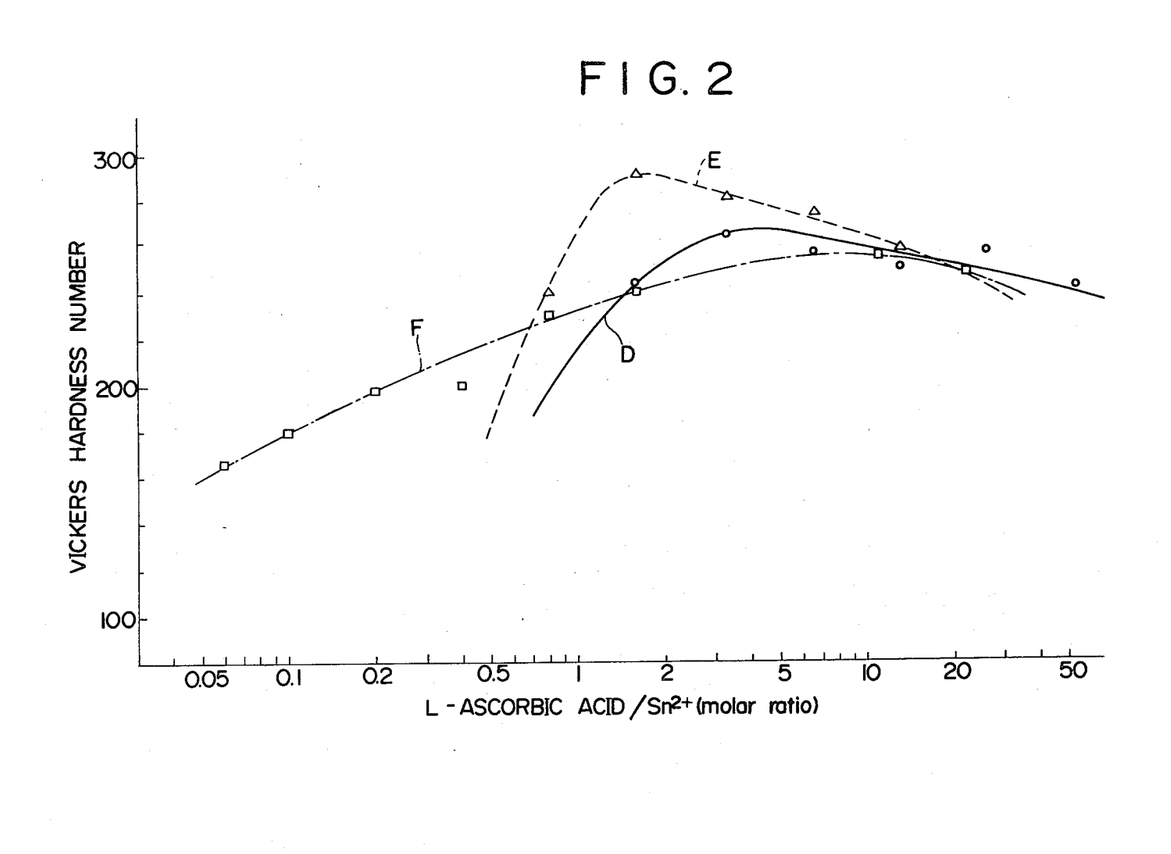
FIG. 2 is a graph showing the relationship between the molar ratios of L-ascorbic acid to stannous ions in the compositions of FIG. 1 and the hardness of the decalcified teeth surfaces treated with these compositions.

| Content of NaF (g) | $F^-/Sn^{2+}$ (molar ratio) | Content of L-ascorbic acid (g) | L-ascorbic acid/$Sn^{2+}$ (molar ratio) | pH of Composition | Hardness (VHN) | Evaluation | Reference mark in FIG. 2 |
|---|---|---|---|---|---|---|---|
| 0.14 | 3.9 | 0.5 | 1.65 | 3.5 | 224 | ⊚ | D |
| | | 1.0 | 3.3 | 3.2 | 265 | ⊚ | |
| | | 2.0 | 6.6 | 2.8 | 257 | ⊚ | |
| | | 3.98 | 13.1 | 2.6 | 250 | ⊚ | |
| | | 7.96 | 26.2 | 2.4 | 257 | ⊚ | |
| | | 12.0 | 40 | 2.4 | 223 | ⊚ | |
| | | 16.0 | 53 | 2.2 | 242 | ⊚ | |

TABLE 3

| Content of $SnF_2$ (g) | Content of NaF (g) | $F^-/Sn^{2+}$ (molar ratio) | Content of L-ascorbic acid (g) | L-ascorbic acid/$Sn^{2+}$ (molar ratio) | pH of Composition | Hardness (VHN) | Evaluation | Reference mark in FIG. 2 |
|---|---|---|---|---|---|---|---|---|
| 1.0 | 0.47 | 3.75 | 0.9 | 0.8 | 3.1 | 240 | ⊚ | E |
| | | | 1.8 | 1.6 | 2.8 | 291 | ⊚ | |
| | | | 3.7 | 3.3 | 2.6 | 281 | ⊚ | |
| | | | 7.3 | 6.5 | 2.4 | 273 | ⊚ | |
| | | | 14.6 | 13.0 | 2.2 | 258 | ⊚ | |

TABLE 3-continued

| Content of SnF$_2$ (g) | Content of NaF (g) | F$^-$/Sn$^{2+}$ (molar ratio) | Content of L-ascorbic acid (g) | L-ascorbic acid/Sn$^{2+}$ (molar ratio) | pH of Composition | Hardness (VHN) | Evaluation | Reference mark in FIG. 2 |
|---|---|---|---|---|---|---|---|---|
| 3.0 | 1.2 | 3.5 | 0.2 | 0.06 | 4.4 | 167 | ∆ | F |
|  |  |  | 0.4 | 0.1 | 4.0 | 180 | ∆ |  |
|  |  |  | 0.7 | 0.2 | 3.4 | 198 | ◎ |  |
|  |  |  | 1.4 | 0.4 | 3.2 | 200 | ◎ |  |
|  |  |  | 2.8 | 0.8 | 2.9 | 230 | ◎ |  |
|  |  |  | 5.5 | 1.6 | 2.7 | 240 | ◎ |  |
|  |  |  | 11 | 3.3 | 2.5 | 255 | ◎ |  |
|  |  |  | 22 | 6.5 | 2.1 | 248 | ◎ |  |

TABLE 4

Figure 3:
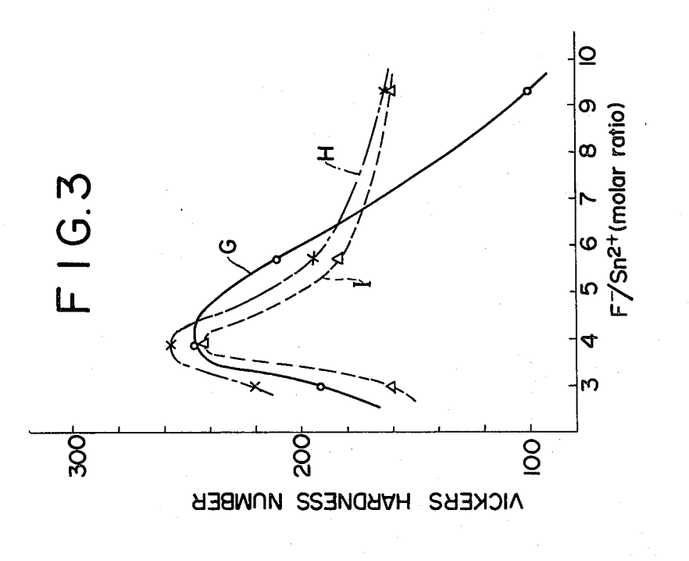
FIG. 3 is a graph showing the relationship between the molar ratios of fluoride ions to stannous ions in the test compositions obtained by dissolving stannous fluoride, sodium fluoride and lactic acid into water and the hardness of the decalcified teeth surfaces treated with these compositions.

| Content of lactic acid (g) | Lactic acid/Sn$^{2+}$ (molar ratio) | Content of NaF (g) | F$^-$/Sn$^{2+}$ (molar ratio) | pH of Composition | Hardness (VHN) | Evaluation | Reference mark in FIG. 3 |
|---|---|---|---|---|---|---|---|
| 3.96 | 25.5 | 0.53 | 9.3 | 2.7 | u.m. | X | G |
| " | " | 0.27 | 5.7 | 2.6 | 210 | ◎ |  |
| " | " | 0.14 | 3.9 | 1.8 | 247 | ◎ |  |
| " | " | 0.07 | 3.0 | 1.5 | 182 | X |  |
| 1.0 | 6.4 | 0.53 | 9.3 | 3.5 | 163 | X | H |
| " | " | 0.27 | 5.7 | 3.0 | 193 | ○ |  |
| " | " | 0.14 | 3.9 | 2.2 | 258 | ◎ |  |
| " | " | 0.07 | 3.0 | 2.0 | 221 | X |  |
| 0.25 | 1.6 | 0.53 | 9.3 | 4.0 | 162 | X | I |
| " | " | 0.27 | 5.7 | 4.0 | 183 | ○ |  |
| " | " | 0.14 | 3.9 | 3.6 | 243 | ◎ |  |
| " | " | 0.07 | 3.0 | 2.8 | 162 | X |  |

Note 1:
"u.m." means that the measurement of hardness was impossible because of destruction of the tooth surface by decalcification.

TABLE 5

Figure 4:
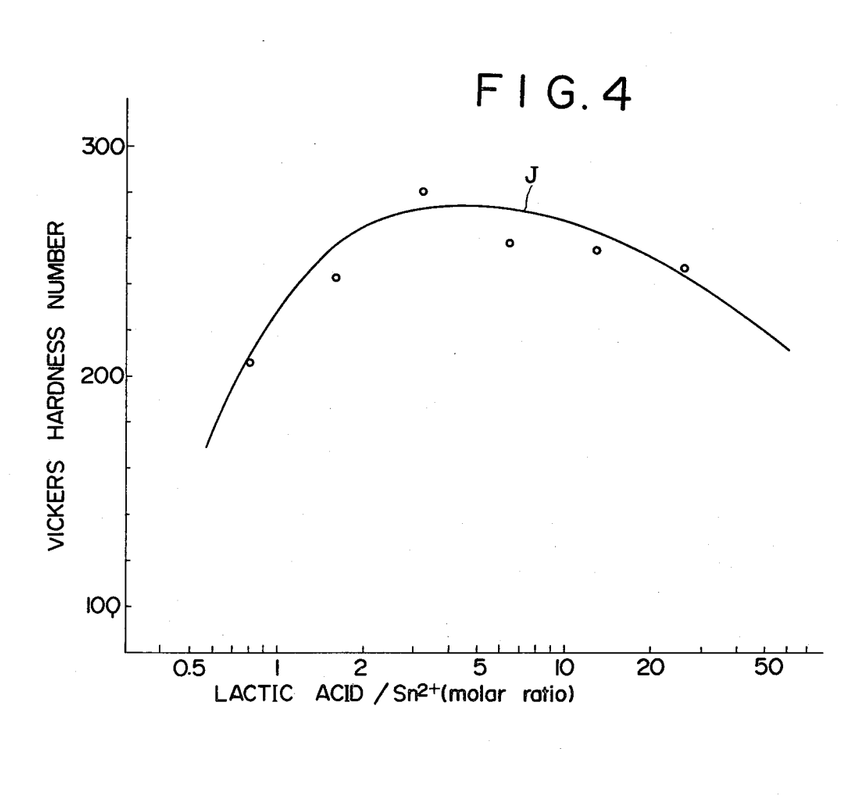
FIG. 4 is a graph showing the relationship between the molar ratios of lactic acid to stannous ions in the compositions of FIG. 3 and the hardness of the decalcified teeth surfaces treated with these compositions.

| Content of NaF (g) | F$^-$/Sn$^{2+}$ (molar ratio) | Content of lactic acid (g) | Lactic acid/Sn$^{2+}$ (molar ratio) | pH of Composition | Hardness (VHN) | Evaluation | Reference mark in FIG. 4 |
|---|---|---|---|---|---|---|---|
| 0.14 | 3.9 | 0.13 | 0.8 | 3.8 | 207 | ◎ | J |
|  |  | 0.25 | 1.6 | 3.6 | 243 | ◎ |  |
|  |  | 0.5 | 3.2 | 2.9 | 280 | ◎ |  |
|  |  | 1.0 | 6.4 | 2.2 | 258 | ◎ |  |
|  |  | 1.98 | 12.8 | 2.0 | 255 | ◎ |  |
|  |  | 3.96 | 25.5 | 1.8 | 247 | ◎ |  |

From the results obtained in Experimental Examples 1 and 2, it was found that the addition of L-ascorbic acid or lactic acid of a monocarboxylic acid group to the mixture of stannous fluoride and sodium fluoride affords a sharp increase in the acid-resistance of dental enamel. Another finding was that the hardness value has a point of change in the vicinity of 3.2 moles of F$^-$ to one mole of Sn$^{2+}$ and the hardness (VHN) of the tooth enamel after decalcification is 200 to 250 in the molar ratio (F$^-$/Sn$^{2+}$) of from 3.2 to 7, preferably from 3.5 to 6.

The same results were obtained with the use of acetic acid, propionic acid, n-butyric acid and gluconic acid instead of L-ascorbic acid and lactic acid.

It was also found that when the monocarboxylic acid is added to the mixture of stannous fluoride and sodium fluoride, its lower molar ratio limit varies with the concentration of stannous ion. Based on this finding, FIG. 5 exemplifies the preferable area in which the monocarboxylic acid performs its effects on the reduction of acid-solubility of the enamel and on the stabilization of stannous ion. In FIG. 5 such area is defined between straight line X$_1$ (M=0.8×0.5$^n$) and straight line X$_3$ (M=30×0.6$^n$), more preferably between straight line X$_2$ (M=0.9×0.6$^n$) and straight line X$_3$, wherein "M" represents the number of moles of the monocarboxylic acid relative to one mole of the stannous ion, and the exponent "n" represents the weight percent of the stannous ion in the composition.

EXPERIMENTAL EXAMPLE 3

100 g of each of some test compositions was prepared by dissolving 0.27 g of stannous fluoride and a predetermined amount of sodium fluoride and malonic acid in water so that the molar ratios of fluoride ions to stannous ions and of the malonic acid to the stannous ions were variable in the compositions. After the procedure of Experimental Example 1 was repeated, the Vickers hardness was measured on sample teeth, and the stability of each of the compositions was determined.

The results obtained are shown in Tables 6 and 7. These results are further illustrated in FIGS. 6 and 7, respectively.

Next, 100 g of each of some test compositions was prepared by dissolving 1.0 g or 3.0 g of stannous fluoride and a given amount of sodium fluoride and malonic acid in water. After sample teeth were treated as above, the Vickers hardness was measured. The results concerning the compositions containing 1.0 g of stannous fluoride are shown in Table 8 and FIG. 7. The results concerning the compositions containing 3.0 g of stannous fluoride are shown in Tables 9 and 10. These results are further illustrated in FIGS. 8 and 7, respectively.

EXPERIMENTAL EXAMPLE 4

100 g of each of some test compositions was prepared by dissolving 0.27 g of stannous fluoride and a given amount of sodium fluoride and tartaric acid in water. After sample teeth were treated as in Experimental Example 1, the Vickers hardness was measured on the sample teeth. The results obtained are shown in Tables 11 and 12. These results are further illustrated in FIGS. 9 and 7, respectively.

TABLE 6

Figure 6:
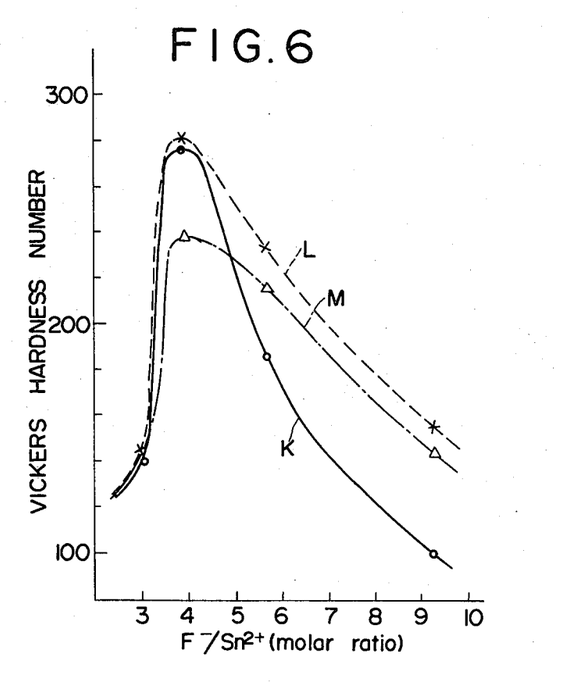
FIG. 6 is a graph showing the relationship between the molar ratios of fluoride ions to stannous ions in the test compositions obtained by dissolving 0.27% of stannous fluoride, sodium fluoride and malonic acid into water and the hardness of the decalcified teeth surfaces treated with these compositions.

| Content of malonic acid (g) | Malonic acid / $Sn^{2+}$ (molar ratio) | Content of NaF (g) | $F^-/Sn^{2+}$ (molar ratio) | pH of Composition | Hardness (VHN) | Evaluation | Reference mark in FIG. 6 |
|---|---|---|---|---|---|---|---|
| 0.29 | 1.6 | 0.53 | 9.3 | 3.1 | u.m. | X | K |
| ″ | ″ | 0.27 | 5.7 | 2.5 | 175 | ○ | |
| ″ | ″ | 0.14 | 3.9 | 2.4 | 277 | ◎ | |
| ″ | ″ | 0.07 | 3.0 | 2.3 | 140 | X | |
| 0.15 | 0.8 | 0.53 | 9.3 | 3.9 | 155 | X | L |
| ″ | ″ | 0.27 | 5.7 | 3.0 | 233 | ◎ | |
| ″ | ″ | 0.14 | 3.9 | 2.8 | 280 | ◎ | |
| ″ | ″ | 0.07 | 3.0 | 2.6 | 145 | X | |
| 0.08 | 0.4 | 0.53 | 9.3 | 4.2 | 143 | X | M |
| ″ | ″ | 0.27 | 5.7 | 3.9 | 215 | ○ | |
| ″ | ″ | 0.14 | 3.9 | 3.4 | 239 | ◎ | |
| ″ | ″ | 0.07 | 3.0 | 2.9 | 143 | X | |

Note 2:
The sample teeth treated with the compositions, in which the molar ratio of fluoride ion to stannous ion is 9.3 and the content of malonic acid is more than 0.29g, were all destructed by calcification, resulting in impossibility of the measurement of hardness.

TABLE 7

Figure 7:
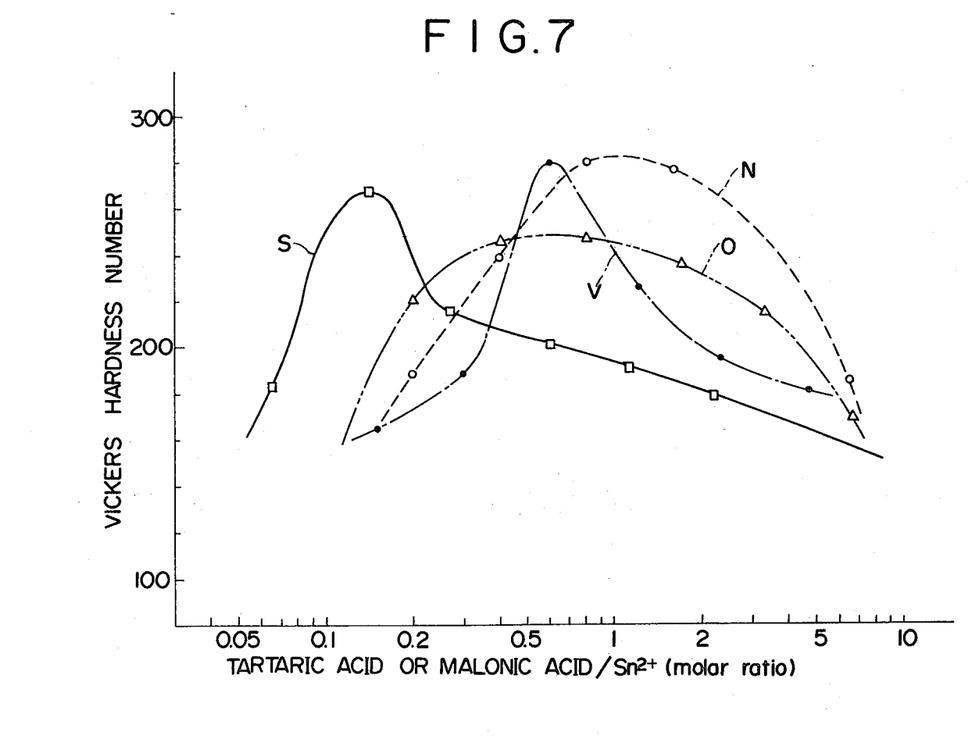
FIG. 7 is a graph showing the relationship between the molar ratios of malonic acid or tartaric acid to stannous ions in the test compositions comprising stannous fluoride, sodium fluoride and the dicarboxylic acid such as malonic acid or tartaric acid and the hardness of the decalcified teeth surfaces treated with these compositions.

| Content of NaF (g) | $F^-/Sn^{2+}$ (molar ratio) | Content of malonic acid (g) | Malonic acid / $Sn^{2+}$ (molar ratio) | pH of Composition | Hardness (VHN) | Evaluation | Reference mark in FIG. 7 |
|---|---|---|---|---|---|---|---|
| 0.14 | 3.9 | 0.04 | 0.2 | 3.6 | 189 | ○ | N |
| | | 0.08 | 0.4 | 3.4 | 239 | ◎ | |
| | | 0.15 | 0.8 | 2.8 | 280 | ◎ | |
| | | 0.29 | 1.6 | 2.4 | 277 | ◎ | |
| | | 0.58 | 3.2 | 2.2 | 248 | ◎ | |
| | | 1.15 | 6.4 | 1.9 | 185 | ○ | |

TABLE 8

| Content of NaF (g) | $F^-/Sn^{2+}$ (molar ratio) | Content of malonic acid (g) | Malonic acid / $Sn^{2+}$ (molar ratio) | pH of Composition | Hardness (VHN) | Evaluation | Reference mark in FIG. 7 |
|---|---|---|---|---|---|---|---|
| 0.47 | 3.75 | 0.14 | 0.2 | 3.2 | 221 | ◎ | O |
| | | 0.27 | 0.4 | 2.8 | 246 | ◎ | |
| | | 0.54 | 0.8 | 2.6 | 247 | ◎ | |
| | | 1.1 | 1.7 | 2.0 | 236 | ◎ | |
| | | 2.2 | 3.3 | 1.6 | 216 | ○ | |
| | | 4.3 | 6.5 | 1.4 | 170 | Δ | |

TABLE 9

Figure 8:
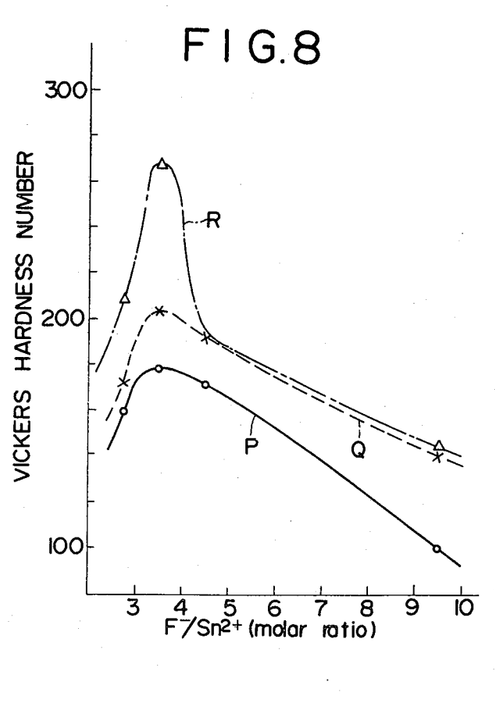
FIG. 8 is a graph showing the relationship between the molar ratios of fluoride ions to stannous ions in the test compositions obtained by dissolving 3% of stannous fluoride, sodium fluoride and malonic acid into water and the hardness of the decalcified teeth surfaces treated with these compositions.

| Content of malonic acid (g) | Malonic acid / $Sn^{2+}$ (molar ratio) | Content of NaF (g) | $F^-/Sn^{2+}$ (molar ratio) | pH of Composition | Hardness (VHN) | Evaluation | Reference mark in FIG. 8 |
|---|---|---|---|---|---|---|---|
| 4.3 | 2.2 | 6 | 9.5 | 2.5 | u.m. | X | P |
| ″ | ″ | 2 | 4.5 | 2.4 | 171 | ○ | |
| ″ | ″ | 1.2 | 3.5 | 1.8 | 178 | ○ | |
| ″ | ″ | 0.6 | 2.75 | 1.4 | 160 | X | |
| 1.1 | 0.6 | 6 | 9.5 | 4.2 | 140 | X | Q |
| ″ | ″ | 2 | 4.5 | 3.2 | 192 | ○ | |
| ″ | ″ | 1.2 | 3.5 | 2.4 | 203 | ◎ | |
| ″ | ″ | 0.6 | 2.75 | 1.8 | 173 | X | |
| 0.27 | 0.14 | 6 | 9.5 | 4.5 | 145 | X | R |
| ″ | ″ | 2 | 4.5 | 4.2 | 193 | ○ | |
| ″ | ″ | 1.2 | 3.5 | 3.1 | 268 | ◎ | |
| ″ | ″ | 0.6 | 2.75 | 2.5 | 208 | X | |

TABLE 10

| Content of NaF (g) | $F^-/Sn^{2+}$ (molar ratio) | Content of malonic acid (g) | Malonic acid / $Sn^{2+}$ (molar ratio) | pH of Composition | Hardness (VHN) | Evaluation | Reference mark in FIG. 7 |
|---|---|---|---|---|---|---|---|
| 1.2 | 3.5 | 0.13 | 0.065 | 3.8 | 184 | ○ | S |
| | | 0.27 | 0.14 | 3.1 | 268 | ◎ | |
| | | 0.54 | 0.27 | 2.8 | 215 | ◎ | |

TABLE 10-continued

| Content of NaF (g) | $F^-/Sn^{2+}$ (molar ratio) | Content of malonic acid (g) | Malonic acid / $Sn^{2+}$ (molar ratio) | pH of Composition | Hardness (VHN) | Evaluation | Reference mark in FIG. 7 |
|---|---|---|---|---|---|---|---|
| | | 1.1 | 0.6 | 2.4 | 203 | ◎ | |
| | | 2.2 | 1.1 | 2.2 | 191 | ○ | |
| | | 4.3 | 2.2 | 2.0 | 178 | △ | |

TABLE 11

Figure 9:
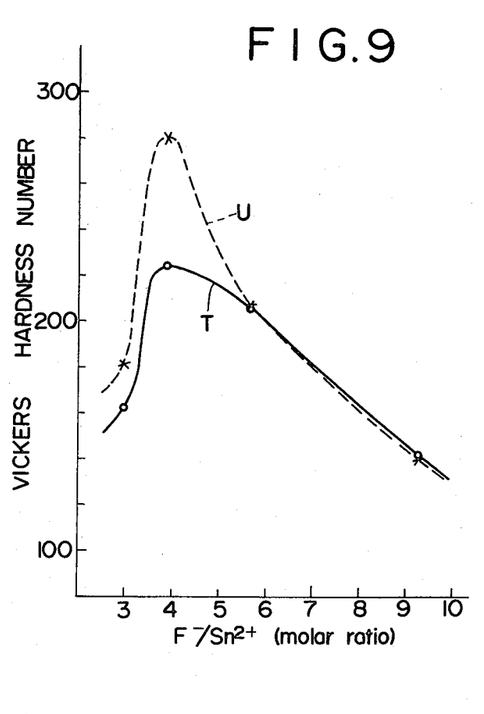
FIG. 9 is a graph showing the relationship between the molar ratios of fluoride ions to stannous ions in the test compositions obtained by dissolving stannous fluoride, sodium fluoride and tartaric acid into water and the hardness of the decalcified teeth surfaces treated with these compositions.

| Content of tartaric acid (g) | Tartaric acid / $Sn^{2+}$ (molar ratio) | Content of NaF (g) | $F^-/Sn^{2+}$ (molar ratio) | pH of Composition | Hardness (VHN) | Evaluation | Reference mark in FIG. 9 |
|---|---|---|---|---|---|---|---|
| 0.32 | 1.2 | 0.53 | 9.3 | 3.0 | 140 | X | T |
| " | " | 0.27 | 5.7 | 2.9 | 206 | ◎ | |
| " | " | 1.14 | 3.9 | 2.6 | 225 | ◎ | |
| " | " | 0.07 | 3.0 | 2.4 | 163 | X | |
| 0.16 | 0.6 | 0.53 | 9.3 | 3.8 | 139 | X | U |
| " | " | 0.27 | 5.7 | 2.8 | 206 | ◎ | |
| " | " | 0.14 | 3.9 | 2.6 | 280 | ◎ | |
| " | " | 0.07 | 3.0 | 2.6 | 182 | X | |

TABLE 12

| Content of NaF (g) | $F^-/Sn^{2+}$ (molar ratio) | Content of tartaric acid (g) | Tartaric acid / $Sn^{2+}$ (molar ratio) | pH of Composition | Hardness (VHN) | Evaluation | Reference mark in FIG. 7 |
|---|---|---|---|---|---|---|---|
| 0.14 | 3.9 | 0.04 | 0.15 | 3.5 | 165 | △ | V |
| | | 0.08 | 0.3 | 3.1 | 188 | ○ | |
| | | 0.16 | 0.6 | 2.6 | 280 | ◎ | |
| | | 0.32 | 1.2 | 2.6 | 225 | ◎ | |
| | | 0.63 | 2.3 | 2.4 | 195 | ○ | |
| | | 1.25 | 4.7 | 2.0 | 181 | ○ | |

From the results obtained in Experimental Examples 3 and 4, it was found that like the monocarboxylic acids, malonic acid or tartaric acid of a dicarboxylic acid group is significantly effective for increasing the resistance to acid-solubility of the enamel in the ratio of from 3.2 to 7 moles of fluoride ion based on one mole of stannous ion.

The same results were obtained with the use of the dicarboxylic acids such as malic acid, succinic acid, maleic acid, L-aspartic acid, L-glutamic acid and oxalic acid, the tricarboxylic acids such as citric acid, and the mineral acids such as hydrochloric acid, sulfuric acid and pyrophosphoric acid.

Figure 10:
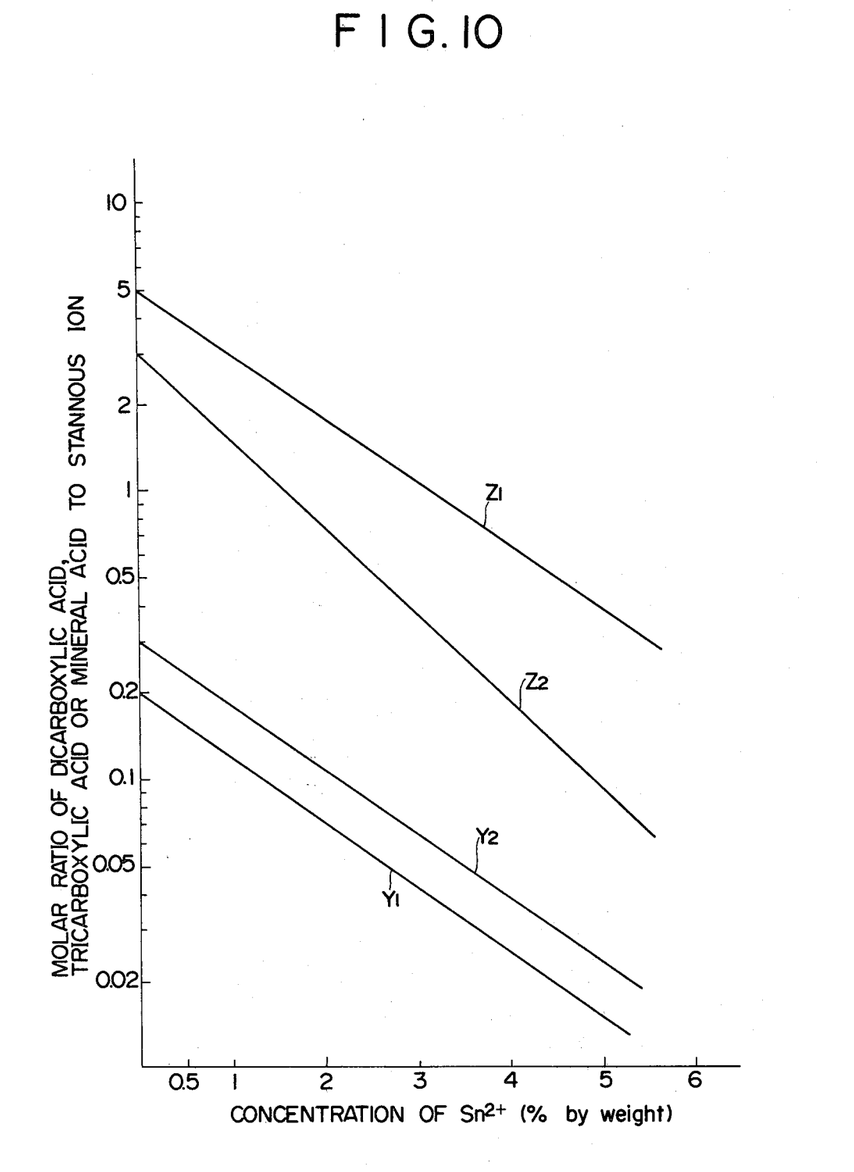
FIG. 10 is a graph showing the preferable range of the molar ratio of dicarboxylic acid, tricarboxylic acid and mineral acid to stannous ions in relation to the concentration of stannous ions.

In FIG. 10 the preferable area in which such acids of the second group (the dicarboxylic acids, the tricarboxylic acids and the mineral acids) perform their effects on acid-resistance of the enamel and on stannous ion stabilization is defined between straight line $Y_1$ ($M=0.2\times0.6^n$) and $Z_1$ ($M=5\times0.6^n$), more preferably between straight line $Y_2$ ($M=0.3\times0.6^n$) and $Z_2$ ($M=3\times0.5^n$).

As is clear from comparison of FIG. 5 to FIG. 10, there is a difference in the lower and upper molar ratio limits of the acids to stannous ion between the case of the monocarboxylic acids and the case of the dicarboxylic acids, tricarboxylic acids and mineral acids.

EXPERIMENTAL EXAMPLE 5

100 g of the test composition according to the present invention was prepared by dissolving 0.205 g of stannous fluoride, 0.11 g of sodium fluoride and 1.2 g of L-ascorbic acid in water.

In the composition sample teeth were immersed at 20° C. for 3 minutes, and then washed with running tap water for 24 hours. After washing, the teeth were treated by the same procedure as in Experimental Example 1, and the Vickers hardness was measured on the samples.

Further, $Ca^{2+}$ ions eluting from the enamel of the tooth were determined by an atomic absorption photometer after the tooth was decalcified with 0.1 M acetic acid buffered solution of pH 4.5 under the same decalcification conditions for hardness measurement as in Experimental Example 1 except that the temperature was 37° C. and the decalcifying time was 5 hours.

Still further, the fluoride uptake by the enamel scraped from the surface to a depth of 3 μm was measured with a fluoride ion electrode after removal of any loosely attached deposits on the tooth by brushing in the same manner as in Experimental Example 1.

Likewise, fresh sample teeth were immersed in the composition at 40° to 50° C. for 3 minutes, and then washed in the above way. The Vickers hardness and $Ca^{2+}$ elution were measured on the thus treated tooth enamel.

For comparative purposes, two aqueous solutions were prepared, one containing 8% (by weight) of stannous fluoride and the other containing acidulated phosphorus fluoride (APF: fluoride ion 1.23% (by weight), pH 3.0). Sample teeth were immersed in these conventional compositions at 20° C. for 3 minutes, and then washed with running tap water for 24 hours. After washing, the teeth were subjected to the measurement of Vickers hardness, $Ca^{2+}$ elution and fluoride ion uptake in the same manner as described above.

The results obtained are shown in Table 13.

In addition to the various experiments, any change in the enamel surface of each of the test teeth after decalcification at 37° C. for 5 hours was observed with a scanning-type electron microscope. FIGS. 11 to 14 are microphotographs showing the results observed and having a magnification of 3,000.

TABLE 13

Figure 11:
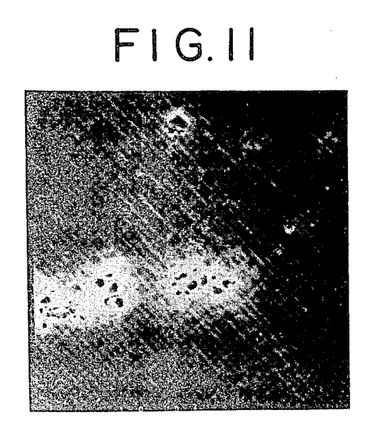
FIGS. 11 to 14 inclusive are microphotographs showing the surface of each of the test teeth after treatment with the present composition and two conventional compositions and subsequently decalcified for comparative purposes, FIG. 11 being directed to one conventional composition comprising a solution of acidulated phosphorus fluoride (APF), FIG. 12 to the other conventional composition comprising an 8% solution of stannous fluoride, and FIGS. 13 and 14 to the embodiments of the invention.
Figure 12:
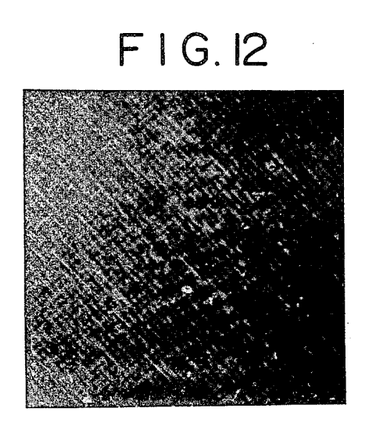
Figure 13:
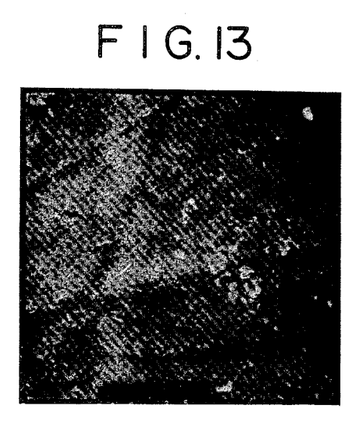
Figure 14:
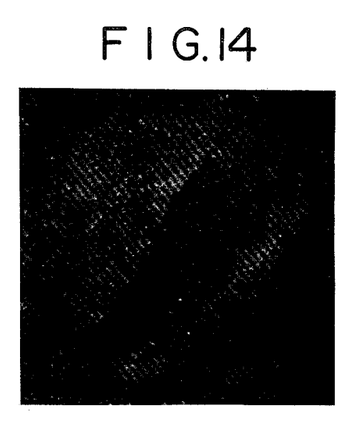

| Immersion Condition | | 20° C., 3 min. | | 40° C.-50° C., 3 min. |
|---|---|---|---|---|
| Test Composition | APF | 8% SnF$_2$ | The Present Composition | The Present Composition |
| Hardness u.m. | 80–100 | 230–240 | 280 | |
| Ca$^{2+}$ Elution (mg/cm$^2$) | 1.0 | 0.9 | 0.4 | 0.4 |
| Fluoride Uptake (ppm) | 300 | 300 | 850 | 3,000 |
| Observation by Electron Microscope | Remarkable Surface Destruction | Remarkable Surface Destruction | None of Surface Destruction | None of Surface Destruction |
| | FIG. 11 | FIG. 12 | FIG. 13 | FIG. 14 |

The sample tooth which was immersed in the present composition at 50° C. for 3 minutes and subsequently washed with running tap water for 2 to 3 minutes demonstrated a value of 15,000 ppm in the fluoride uptake measured in the same manner as above.

A careful consideration of all of the results obtained in this Experimental Example indicates that the oral composition according to the present invention gives high resistance to acid-solubility and increased fluoride uptake to the dental enamel, and hence gives surprisingly remarkable activities on the inhibition of dental caries.

EXPERIMENTAL EXAMPLE 6

Some test compositions were prepared by dissolving stannous fluoride and sodium fluoride together with the acid tabulated in Table 14 in water such that the pHs of the compositions became 2.6. After storage of the compositions at room temperature for one month in an open or closed state, the dissolved stannous ions were quantitatively measured by an iodometric titration and the remaining rate of the dissolved stannous ions in the compositions was calculated.

The results obtained are shown in Table 14.

TABLE 14

| Remaining Rate of Dissolved Stannous Ion | | | | |
|---|---|---|---|---|
| Storage Condition | Closed | | Open | |
| Concentration of Stannous Fluoride (just prepared) | 0.205% | 3% | 0.205% | 3% |
| NaF/SnF$_2$ (Molar ratio) | 2 | 1.5 | 2 | 1.5 |
| Acid L-ascorbic acid | Nearly 100% | 100% | 100% | 100% |
| Gluconic acid | " | " | 20% | 85% |
| Lactic acid | " | " | 10% | 60% |
| Malonic acid | " | " | 10% | 65% |
| Tartaric acid | " | " | 10% | 60% |
| Citric acid | " | " | 10% | 65% |

These test compositions did not become cloudy nor furnish any precipitants even after a six-month storage in the closed state. In contrast, acid-free compositions produced precipitants within half a day in a stannous ion content of 0.205% (by weight), and within five days in that content of 3% (by weight).

The followng specific examples are further illustrative of the present invention, but it is to be understood that the invention is not limited thereto. All amounts of the various ingredients are by weight unless otherwise specified.

EXAMPLE 1

| Topical Solution for Dental Use | |
|---|---|
| Stannous fluoride | 3.0% |
| Sodium fluoride | 1.2% |
| Gluconic acid | 2.0% |
| Flavor | 0.5% |
| Saccharin | 0.02% |
| Water | Balance |
| | 100.0% |

A topical solution was prepared by dissolving the ingredients into water.

EXAMPLE 2

| Topical Solution for Dental Use | |
|---|---|
| Stannous chloride | 3.6% |
| Sodium fluoride | 2.0% |
| Gluconic acid | 2.0% |
| Flavor | 0.5% |
| Saccharin | 0.02% |
| Water | Balance |
| | 100.0% |

A topical solution was prepared in the same manner as Example 1.

EXAMPLE 3

| Topical Paste for Dental Use | |
|---|---|
| Stannous fluoride | 0.205% |
| Sodium fluoride | 0.110% |
| L-ascorbic acid | 1.2% |
| Flavor | 0.5% |
| Saccharin | 0.15% |
| Propylene glycol | 5.0% |
| Sorbitol | 10.0% |
| Xanthane gum | 2.5% |
| Ethyl para-hydroxybenzoate | 0.001% |
| Water | Balance |
| | 100.0% |

Stannous fluoride, sodium fluoride and L-ascorbic acid were dissolved into 50 parts of water. This solution was mixed with the solution obtained by dissolving the other ingredients into 50 parts of water to prepare a topical paste.

EXAMPLE 4

| Gel for Ultrasonic Treatment | |
|---|---|
| Stannous fluoride | 1.0% |
| Sodium fluoride | 0.47% |
| L-ascorbic acid | 1.5% |
| Flavor | 0.5% |
| Saccharin | 0.1% |
| Propylene glycol | 6% |
| Glycerin | 15% |
| Guar gum | 2.5% |
| Butyl para-hydroxybenzoate | 0.01% |
| Water | Balance |
| | 100.0% |

A gel for ultrasonic treatment was prepared as Example 3.

EXAMPLE 5

| Mouthwash | |
|---|---|
| Stannous fluoride | 0.205% |
| Sodium fluoride | 0.110% |
| Pyrophosphoric acid | 0.2% |
| Flavor | 0.50% |
| Saccharin | 0.10% |
| Water | Balance |
| | 100.0% |

A mouthwash was prepared by dissolving the ingredients into water.

EXAMPLE 6

| Toothpaste | |
|---|---|
| Insoluble sodium metaphosphate | 40% |
| Sorbitol | 10% |
| Glycerin | 10% |
| Propylene glycol | 3.0% |
| Carrageenan | 0.5% |
| Carboxymethyl cellulose | 0.6% |
| Saccharin | 0.1% |
| Ethyl para-hydroxybenzoate | 0.01% |
| Flavor | 1.0% |
| Sodium lauryl sulfate | 2.0% |
| Anhydride silica | 3.0% |
| Stannous fluoride | 0.27% |
| Sodium fluoride | 0.145% |
| Lactic acid | 1.0% |
| Water | Balance |
| | 100.0% |

Stannous fluoride, sodium fluoride and lactic acid were dissolved into some water. This solution was mixed with the paste obtained by blending the other ingredients with the remaining water to prepare a toothpaste.

EXAMPLE 7

| Toothpaste | |
|---|---|
| Insoluble sodium metaphosphate | 45% |
| Sorbitol | 20% |
| Propylene glycol | 3.0% |
| Xanthane gum | 1.0% |
| Saccharin | 1.0% |
| Butyl para-hydroxybenzoate | 0.005% |
| Flavor | 1.0% |
| Sodium lauryl sulfate | 2.0% |
| Anhydride silica | 3.0% |
| Stannous fluoride | 0.27% |
| Sodium monofluorophosphate | 0.50% |
| Malonic acid | 0.2% |
| Water | Balance |
| | 100.0% |

A toothpaste was prepared in the same manner as in Example 6.

What is claimed is:

1. An oral composition for caries prophylaxis comprising a stannous salt, a water-soluble fluoride salt selected from the group consisting of sodium fluoride, potassium fluoride and mixtures thereof, and an orally acceptable acid selected from the group consisting of a monocarboxylic acid, a dicarboxylic acid, a tricarboxylic acid, a mineral acid and mixtures thereof, said stannous salt being present in the range of from 0.07% by weight of the total amount of the composition as stannous ion to the saturated state in water, the molar ratio of fluoride ion to stannous ion being in the range of from 3.5:1 to 5.7:1 in the aqueous condition, the molar ratio of said monocarboxylic acid to stannous ion being in the range of from $0.8 \times 0.5^n:1$ to $30 \times 0.6^n:1$, the exponent "n" being the weight percent content of the stannous ion in the composition, and said orally acceptable acid being present in the composition in such an amount that the pH of the composition is in the range of from 2 to 4.

2. An oral composition for caries prophylaxis comprising a stannous salt, a water-soluble fluoride salt selected from the group consisting of sodium fluoride, potassium fluoride and mixtures thereof, and an orally acceptable acid selected from the group consisting of a monocarboxylic acid, a dicarboxylic acid, a tricarboxylic acid, a mineral acid and mixtures thereof, said stannous salt being present in the range of from 0.07% by weight of the total amount of the composition as stannous ion to the saturated state in water, the molar ratio of fluoride ion to stannous ion being in the range of from 3.5:1 to 5.7:1 in the aqueous condition, the molar ratio of the acid selected from the group consisting of a dicarboxylic acid, a tricarboxylic acid and a mineral acid to stannous ion being in the range of from $0.2 \times 0.6^n:1$ to $5 \times 0.6^n:1$, the exponent "n" being the weight percent content of the stannous ion in the composition, and said orally acceptable acid being present in the composition in such an amount that the pH of the composition is in the range of from 2 to 4.

3. The oral composition according to claim 1 or 2, wherein said stannous salt is at least one member selected from the group consisting of stannous fluoride, stannous chloride, stannous chlorofluoride, stannous pyrophosphate, stannous monofluorophosphate and stannous acetate.

4. The oral composition according to claim 1 or 2, wherein said stannous salt is stannous fluoride.

5. The oral composition according to claim 1, wherein said monocarboxylic acid is selected from the group consisting of L-ascorbic acid, lactic acid, acetic acid, propionic acid, n-butyric acid, gluconic acid and mixtures thereof.

6. The oral composition according to claim 2, wherein said dicarboxylic acid is selected from the group consisting of malonic acid, tartaric acid, malic acid, succinic acid, maleic acid, L-aspartic acid, L-glutamic acid, oxalic acid and mixtures thereof.

7. The oral composition according to claim 2, wherein said tricarboxylic acid is citric acid.

8. The oral composition according to claim 2, wherein said mineral acid is selected from the group consisting of hydrochloric acid, sulfuric acid, orthophosphoric acid, pyrophosphoric acid and mixtures thereof.

* * * * *